(12) United States Patent
Jones et al.

(10) Patent No.: US 10,441,725 B2
(45) Date of Patent: Oct. 15, 2019

(54) DOSE SETTING MECHANISM FOR A DRUG DELIVERY DEVICE AND DRUG DELIVERY DEVICE

(71) Applicant: Sanofi-Aventis Deutschland GmbH, Frankfurt am Main (DE)

(72) Inventors: Matthew Meredith Jones, Warwickshire (GB); Samuel Keir Steel, Warwickshire (GB); Neal Alexander Blundred, West Midlands (GB); Joseph Butler, Warwickshire (GB); Robert Frederick Veasey, Warwickshire (GB); David Plumptre, Worcestershire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 284 days.

(21) Appl. No.: 15/313,905

(22) PCT Filed: May 27, 2015

(86) PCT No.: PCT/EP2015/061632
§ 371 (c)(1),
(2) Date: Nov. 23, 2016

(87) PCT Pub. No.: WO2015/181195
PCT Pub. Date: Dec. 3, 2015

(65) Prior Publication Data
US 2017/0189622 A1    Jul. 6, 2017

(30) Foreign Application Priority Data

May 28, 2014 (EP) .................................... 14170378

(51) Int. Cl.
*A61M 5/19* (2006.01)
*A61M 5/24* (2006.01)
(Continued)

(52) U.S. Cl.
CPC .......... *A61M 5/31596* (2013.01); *A61M 5/19* (2013.01); *A61M 5/2448* (2013.01);
(Continued)

(58) Field of Classification Search
CPC ................ A61M 5/31596; A61M 5/19; A61M 5/31528; A61M 5/31551;
(Continued)

(56) References Cited

U.S. PATENT DOCUMENTS

2013/0253440 A1* 9/2013 Smith ............... A61M 5/31565
604/246
2013/0267908 A1* 10/2013 Leak ...................... A61M 5/19
604/191
(Continued)

FOREIGN PATENT DOCUMENTS

| WO | WO 2012/072533 | 6/2012 |
| WO | WO 2012/072541 | 6/2012 |
| WO | WO 2012/072554 | 6/2012 |

OTHER PUBLICATIONS

International Preliminary Report on Patentability in International Application No. PCT/EP2015/061632, dated Nov. 29, 2016, 7 pages.
(Continued)

*Primary Examiner* — Bhisma Mehta
*Assistant Examiner* — William R Frehe
(74) *Attorney, Agent, or Firm* — Fish & Richardson P.C.

(57) ABSTRACT

A dose setting mechanism for a drug delivery device includes a primary drug delivery assembly and a secondary drug delivery assembly. The dose setting mechanism includes a primary dose dial component for setting a dose in the primary drug delivery assembly and a secondary dose dial component for setting a dose in the secondary drug delivery assembly. The primary dose dial component and the
(Continued)

secondary dose dial component are configured to rotate during dose setting. A gear mechanism is configured such that in a first phase of the dose setting, rotation of the primary dose dial component is transferred to the secondary dose dial component and such that in a second phase of the dose setting, the secondary dose dial component is decoupled from the primary dose dial component such that rotation of the primary dose dial component is prevented from being transferred to the secondary dose dial component.

19 Claims, 7 Drawing Sheets

(51) Int. Cl.
    *A61M 5/31*     (2006.01)
    *A61M 5/315*     (2006.01)
    *A61M 5/32*     (2006.01)
    *A61M 5/178*     (2006.01)

(52) U.S. Cl.
    CPC ...... *A61M 5/3146* (2013.01); *A61M 5/31528* (2013.01); *A61M 5/31538* (2013.01); *A61M 5/31551* (2013.01); *A61M 5/31575* (2013.01); *A61M 5/31591* (2013.01); *A61M 5/31593* (2013.01); *A61M 5/3295* (2013.01); *A61M 2005/1787* (2013.01); *A61M 2005/3126* (2013.01); *A61M 2205/581* (2013.01); *A61M 2205/582* (2013.01)

(58) Field of Classification Search
    CPC .... A61M 2005/1787; A61M 2205/582; A61M 2005/31598; A61M 5/2066; A61M 5/31526; A61M 2005/3152; A61M 5/3155; A61M 5/31553; A61M 5/31555
    See application file for complete search history.

(56) References Cited

U.S. PATENT DOCUMENTS

| | | | |
|---|---|---|---|
| 2014/0257194 A1* | 9/2014 | Edhouse | A61M 5/20 604/198 |
| 2014/0303560 A1* | 10/2014 | Yates | A61M 5/1407 604/154 |
| 2016/0220759 A1* | 8/2016 | Enggaard | A61M 5/31541 |
| 2017/0080161 A1* | 3/2017 | Jones | A61M 5/19 |
| 2017/0136190 A1* | 5/2017 | Jones | A61M 5/19 |
| 2017/0165430 A1* | 6/2017 | Holtwick | A61M 5/19 |
| 2017/0239422 A1* | 8/2017 | Kodgule | A61M 5/19 |

OTHER PUBLICATIONS

International Search Report and Written Opinion in International Application No. PCT/EP2015/061632, dated Aug. 5, 2015, 10 pages.

* cited by examiner

DOSE SETTING MECHANISM FOR A DRUG DELIVERY DEVICE AND DRUG DELIVERY DEVICE

CROSS-REFERENCE TO RELATED APPLICATIONS

This application is a National Stage application under 35 U.S.C. § 371 of International Application No. PCT/EP2015/061632, filed May 27, 2015, which claims the benefit of EP Application No. 14170378.5, filed on May 28, 2014. The disclosures of the prior applications are incorporated by reference in their entirety.

TECHNICAL FIELD

The present disclosure is directed to a dose setting mechanism for drug delivery device with a primary drug delivery assembly and a secondary drug delivery assembly.

BACKGROUND

Certain disease states require treatment using one or more different medicaments. Some drug compounds need to be delivered in a specific relationship with each other in order to deliver the optimum therapeutic dose. Here, combination therapy may be desirable, but not possible in a single formulation for reasons such as, but not limited to, stability, compromised therapeutic performance and toxicology.

For example, in some cases it might be beneficial to treat a diabetic with a long acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus. Another example of a medicament combination is the administration of a pain reliever in combination with a medicament for treating osteoarthritis.

Drug delivery devices of the aforementioned kind often have applications where regular injection by persons without formal medical training occurs. This is increasingly common among patients having diabetes or the like, e.g. osteoarthritis. Self-treatment enables such patients to conduct effective management of their disease.

In combination therapy, a primary medicament and a secondary medicament are delivered in a specific relationship to deliver the optimum therapeutic dose. The injection devices of the generic kind usually comprise a housing or a housing assembly in which two or more drug delivery assemblies are retained. Such devices include a primary drug delivery assembly for dispensing the primary medicament such as the long-acting insulin and a secondary drug delivery assembly for dispensing the secondary medicament, such as GLP-1. Some kinds of drug delivery assemblies comprise a compartment such as a cartridge holder for accommodating a replaceable medicament container such as a cartridge which stores the medicament.

In some cases, depending on the patient or the stage of the therapy, an effective treatment requires variations in the quantities and/or proportions of the medicaments making up the combined therapy. For example, the patient may require a non-adjustable fixed dose of the secondary medicament in combination with an adjustable variable dose of the primary medicament. The primary medicament and the secondary medicament are each contained in a single cartridge.

The effectiveness of a combined delivery of medicaments may require one or more doses to be delivered sequentially with one of the two medicaments being injected into the human body prior to the delivery of the other medicament. Such treatment may be conducted with devices that include two separate dispensing mechanisms that are actuated independently from each other such that the dispensing mechanisms are activated successively. Sometimes patients require merely a dose of one of the medicaments, e.g. the primary medicament. The correct use of the device, however, may be hazardous for patients that are physically or mentally impaired or otherwise disadvantaged.

From WO 2012/072554 A1, a drug delivery device is known that comprises a variable dose setting mechanism coupled to a drive gear that is coupled to a driven gear of a fixed dose setting mechanism. The driven gear is fixed axially and rotationally to a worm gear that interfaces with a sprung rack such that rotation of the worm gear forces the sprung rack upwards against a spring. The drive gear comprises vertical splines on an inner portion of the drive gear. The variable dose setting mechanism engages with the first gear via the engagement of drive features of a drive sleeve with the vertical splines the drive gear until a certain dose of a second medicament is set by the fixed dose mechanism. Then, the drive features on the drive sleeve disengage from the vertical splines and allow the variable dose setting mechanism to set larger doses without further rotation of the driven gear.

A similar mechanism is described in WO 2012/072533 A1, where the mechanical coupling between a fixed dose setting mechanism and a variable dose setting mechanism includes a drive sleeve that disengages from a drive gear after a fixed dose of a second medicament is set.

WO 2012/072541 A1 describes a drug delivery device with a variable and a fixed dose setting mechanism interlinked by a mechanical coupling. The mechanical coupling includes a lift cylinder, a lifting collar and an engagement pin. The variable dose setting mechanism is rotated and the lifting collar is in engagement with the lift cylinder via the engagement pin. The stroke length where the lifting collar is in engagement with the lift cylinder is sufficient to lift the cylinder which in turn sets the fixed dose setting mechanism and stores energy with a spring. When the lifting collar disengages from the engagement pin, it is allowed to continue on its path to set a larger dose of the variable dose medicament.

SUMMARY

Certain aspects of the present invention provide the setting capabilities of a drug delivery device of the aforementioned kind and provide for a device that is simple in terms of use and that has a high degree of user safety. Certain aspects provide for an improved dose setting mechanism to set a variable dose of the primary medicament in combination with a fixed dose of the secondary medicament. Moreover, the user can prime his device with the primary medicament without using any fixed dose medicament.

The proposed mechanism enables the user to set a variable dose of the primary medicament in the primary drug delivery assembly to the required dosage quantity. Accordingly, the primary drug delivery assembly may be designed as a variable dose mechanism. The dose setting procedure includes two consecutive phases. By coupling the primary dose dial component and the secondary dose dial component during the first phase, the setting movement of the primary dose dial component to set a dose of the primary medicament is transferred to the secondary dose dial component such that a dose of the secondary medicament is automatically set in the secondary drug delivery assembly. The amount of the set dose in the secondary drug delivery assembly cannot be influenced by the user.

The gear mechanism is configured such that in the second phase, the secondary dose dial component is decoupled from the primary dose dial component such that dose setting in the secondary drug delivery assembly is stopped. Accordingly, the amount of the set dose of the secondary medicament depends on the rotational displacement of the primary dose dial component. In other words, the gear mechanism is designed such that the primary dose dial component decouples from the secondary dose dial component after a predetermined displacement of the primary dose dial component. As a result, a predetermined fixed dose of the secondary medicament is set in the secondary drug delivery assembly. Accordingly, the secondary drug delivery assembly may be designed as a fixed dose mechanism. This provides for improved safety characteristics as the user is not required to the set fixed dose. Instead, the user can receive a constant predetermined fixed dose of the secondary medicament when he sets his variable dose of the primary medicament depending on his needs. Operating errors are virtually eliminated and the user can focus on setting the variable dose of medicament.

The term "fixed dose" as used herein can be characterized as a dose value that is defined by the construction of the drug delivery assembly or the drug delivery device, wherein the user is only able to inject a specific dose. The user is not in the position to set lower or higher doses of medicament and/or to inject lower or higher doses of the medicament. The dose the user may effectively set and inject is restricted to a certain value.

On the contrary, the term "variable dose" can be characterized as a dose where the user is substantially free to choose the amount of medicament he wants to inject. The dose is variably adjustable, normally between upper and lower limits.

In particular, the proposed dose setting mechanism is designed for drug delivery devices which comprise a primary drug delivery assembly configured for the delivery of a primary medicament from a primary medicament cartridge and which comprise a secondary drug delivery assembly configured for the delivery of a secondary medicament contained in a secondary medicament cartridge. Each of the drug delivery assemblies is accommodated in a drug delivery device housing or housing assembly that extends from a proximal end to a distal end along a longitudinal axis and that accommodates the primary and the secondary drug delivery assembly, which may extend along a longitudinal axis each, said axis being parallel offset to the longitudinal axis of the drug delivery device. Preferably, the primary dose dial component and the secondary dose dial component are configured to rotate about a respective rotational axis, the axes of rotation being arranged in a parallel relationship.

The distal end is usually referred to as the dispensing end where the drug delivery device may be equipped with a single dispense interface, such as a needle hub with an injection needle. The proximal end may be referred to as the setting end where a user operates a dose dial grip or the like to set medicament doses. The dose dial grip may be rotationally coupled to the primary dose dial component during dose setting.

The housing assembly may comprises two sub-assemblies, one accommodating the primary drug delivery assembly and one accommodating the secondary drug delivery assembly, wherein the sub-assemblies are configured for mutual attachment.

The primary medicament, e.g. a long-acting insulin, may be contained in primary reservoir that may be configured to be coupled to the primary drug delivery assembly which may include a lead screw, a piston rod or the like that moves in distal direction during dose dispense and that urges a bung in the primary reservoir distally such that the primary medicament is dispensed. The secondary medicament, e.g. GLP-1, may be contained in a secondary reservoir that may be configured to be coupled to the secondary drug delivery assembly which may include a lead screw, a piston rod or the like that moves in distal direction during dose dispense and that urges a bung in the secondary reservoir distally such that the secondary medicament is dispensed. Accordingly, two cartridges can be coupled to the drug delivery device.

It has been proven effective, when the primary dose dial component is configured as a dose dial sleeve or a number sleeve. In particular, the primary dose dial component may be in threaded engagement with the housing assembly. The primary dose dial component may engage the housing assembly by a helical thread. For example, the outer surface of the primary dose dial component may be provided with a groove following a helical path on the outer surface of the primary dose dial component. Said groove may be engaged by an inner thread feature of the housing assembly so that rotation of the primary dose dial component causes the primary dose dial component to move in axial direction relative to the housing assembly. The primary dose dial component may at least partially be provided in the housing assembly. Depending on the direction the primary dose dial component is rotated, the primary dose dial component displaces in proximal direction (preferably during dose setting) or in distal direction (preferably during dose dispense).

According to a further embodiment, the dose setting mechanism comprises a first gear or first gear wheel that is coupled to the primary dose dial component in such way that in the first phase of the dose setting until a predetermined rotational and/or axial displacement of the primary dose dial component, the primary dose dial component is rotationally locked to the first gear and such that in the second phase of the dose setting, the primary dose dial component is rotationally decoupled from the first gear. This structure provides for a very reliable transmission mechanism. In comparison to regular gear mechanisms comprising a first and a second gear, not the gears are decoupled from each other but the connection between the first gear and the primary dose dial component. Thereby precision of the gear mechanism is maintained even after a long-time use.

According to a further embodiment, the dose setting mechanism comprises a second gear or gear wheel which is in meshed engagement with the first gear and that is rotationally coupled to the secondary dose dial component during dose setting. By providing a first and a second gear, different transmission ratios can be realized so that the secondary dose dial component rotates at a predetermined ratio with respect to the primary dose dial component, when the primary dose dial component is rotated. For example, the primary drug delivery assembly may have a mechanical advantage of 3.08:1 with respect to the secondary drug delivery assembly. The transmission mechanism guarantees a very precise setting regarding the fixed dose of the secondary medicament.

In order to provide a precise decoupling of the primary dose dial component from the first gear, the first gear may comprise a boss that is engaged with a track or a groove on the primary dose dial component to transfer rotation between the primary dose dial component and the first gear.

The first gear may comprise a sleeve-like element that at least partly surrounds the primary dose dial component, wherein the inner surface of the first gear is provided with said boss. The track may be provided on an outer peripheral surface of the primary dose dial component and may be formed as a groove or the like. By the engagement between the track and the boss, rotation between the primary dose dial component and the first gear is effectively transferred.

In order to provide for a precise decoupling and control of the movement of the first gear, the track may comprise a first section and a second section, wherein the boss is engaged with the first section until a predetermined variable dose is set, respectively after a predetermined rotation of the primary dose dial component. Alternatively or in addition, the boss is engaged with the first section until a predetermined fixed dose is set with the secondary dose dial component, respectively until the second dose dial component is rotated a predetermined rotational way. The second section may be adapted such that engagement of the boss with the second section rotationally decouples the primary dose dial component from first gear.

A further embodiment refers to a dose setting mechanism for a drug delivery device comprising a primary drug delivery assembly and a secondary drug delivery assembly, wherein the dose setting mechanism comprises a primary dose dial component for setting a dose in the primary drug delivery assembly and a secondary dose dial component for setting a dose in the secondary drug delivery assembly, wherein the primary dose dial component and the secondary dose dial component are configured to rotate during dose setting. A gear mechanism is included that comprises a first gear coupled to the primary dose dial component and a second gear that is in meshed engagement with the first gear and that is rotationally coupled to the secondary dose dial component during dose setting, wherein the first gear comprises a boss engaged with a track on the primary dose dial component to transfer rotation between the primary dose dial component and the first gear. The track comprises a first section and a second section, wherein the boss is engaged with the first section in a first phase of the dose setting such that the primary dose dial component is rotationally locked to the first gear and rotation of the primary dose dial component is transferred to the secondary dose dial component such that a dose in the secondary drug delivery assembly is automatically set. The boss is engaged with the first section until a predetermined dose is set with the primary dose dial component and/or with the secondary dose dial component, wherein the boss is engaged with the second section (in a second phase of the dose setting) after the predetermined dose is dialed with the primary dose dial component and/or with the secondary dose dial component, wherein the second section is adapted such that engagement of the boss with the second section rotationally decouples the primary dose dial component from the first gear such that in a second phase of the dose setting, rotation of the primary dose dial component is prevented from being transferred to the secondary dose dial component.

By engaging or entering the second section from the first section, the boss rotationally decouples the first gear from the primary dose dial component because rotation cannot be transferred between the boss and the track in the second section. The boss remains engaged with the first track during the first phase of the dose setting. In particular, the primary dose dial component may be configured to move relative to the boss in axial direction during dose setting such that after a predetermined axial travel of the primary dose dial component relative to the first gear, the boss leaves the first section—at which point the fixed dose setting is accomplished—and enters the second section of the track such that the boss is rotationally decoupled from the primary dose dial component and the primary dose dial component is free to rotate relative to the boss.

By efficiently preventing the transfer of rotational movement from the primary dose dial component to the secondary dose dial component, an increasing dose can be set in the primary drug delivery assembly, while the set dose in the secondary drug delivery assembly remains at the dose set in the first phase of the dose setting.

According to a further embodiment, the first section is configured as to form an axially extending key or splined connection with the boss. The first section may comprise an axially extending track or groove, extending substantially parallel to the rotational axis of the primary dose dial component, wherein the primary dose dial component is able to move axially with respect to the first gear.

The first and the second section may be formed such that they have a different pitch in axial direction. The first section may include the above described axially extending groove while the second section may be provided with a wide track or the like without an abutment for the boss when the track rotates relative to the boss, thereby rotationally decoupling the first gear from the primary dose dial component.

The second section may extend along a helical path on the outer surface of the primary dose dial component. The helical path of the second section may regarding its pitch correspond to the helical path of the thread engagement between the primary dose dial component and the housing assembly such that when the primary dose dial component is rotated, the helical path of the second section moves along the boss without causing the boss to rotate.

According to a further embodiment, the primary dose dial component is rotationally connected or fixed to a primary drive sleeve during dose setting. The primary drive sleeve is configured for driving a secondary lead screw in distal direction, preferably by translating in distal direction, wherein the primary drive sleeve is in threaded engagement with the primary lead screw or piston rod via a first thread.

The primary lead screw may be in threaded engagement with the housing assembly via a second thread. The first and the second thread have opposite hands wherein the ratio between the pitches of the threads determines the mechanical advantage of the variable dose mechanism. The thread between the primary drive sleeve and the primary lead screw preferably has an identical pitch to the thread between the primary dose dial component and the housing assembly.

A very a precise setting can be achieved when the secondary dose dial component is configured as a secondary drive sleeve for driving a secondary lead screw in distal direction preferably by movement in distal direction. The secondary drive sleeve may be in threaded engagement with the secondary lead screw via a first thread, wherein the secondary lead screw is in threaded engagement with the housing assembly via a second thread. The first and the second thread may have opposite hands.

The pitch of the thread between the secondary drive sleeve and the secondary lead screw may be equal to the pitch of the thread between the primary drive sleeve and the primary lead screw divided by the ratio between the first gear and the second gear. This mathematical relationship ensures that actuation elements provided to force the primary drive sleeve and the secondary drive sleeve in distal direction during dose dispense maintain a relative vertical position during setting and dispensing. Thereby, a common actuator can easily be implemented.

In order to ensure that a fixed dose is only set when a minimum dose of the primary medicament is set, a further embodiment provides that the secondary dose dial component comprises a helical track engaged by at least one thread feature of the housing, wherein the secondary dose dial component comprises at least one angled track or angled path intersecting the helical track, wherein the angled track is arranged such that after dose setting, the thread feature is guided along the angled track under an axial force in distal direction applied to the secondary dose dial component. In other words, the angled track is arranged such that the thread feature is positioned at the angled track after the first phase of the dose setting such that an axial force applied to the secondary dose dial component guides the thread feature into the angled track. This mechanism efficiently ensures that a fixed dose is only set when a minimum dose of the primary medicament is set, respectively when the secondary dose dial component is rotated at least at a predetermined distance. Preferably, the angled track extends in axial direction of the secondary dose dial component and forms a splined interface with the thread feature.

The dose setting mechanism can be designed such that the user may dial and dispense a prime dose of e.g. 2 units of the primary medicament without any fixed dose medicament. For this purpose, the angled track may be arranged such that the secondary dose dial component is forced to rotate in a direction opposite the setting direction thereby unsetting the set fixed dose. The thread feature is forced to travel in the helical track to a starting position corresponding to a set dose of zero units when the thread feature is not brought into alignment with the angled track and an axial force in distal direction is applied to the secondary dose dial component.

The coupling between the first gear and the primary dose dial component may designed such that the first gear decouples from the primary dose dial component when the thread feature aligns with the at least one angled track or has passed the intersection. This ensures that the fixed dose element is fully set before the first gear disengages the primary dose dial component and stops rotating the secondary dose dial component.

Sequential delivery may be improved, when the angled track is arranged with respect to the helical track such that the tread feature re-engages the helical track during dispense of the secondary medicament such that the secondary dose dial component is forced to rotate in an unsetting movement, when an axial force in distal direction is applied to the secondary dose dial component.

In order to ensure the guidance of the thread feature into the at least one angled track, the helical track may comprise at least one detent feature arranged between the angled track and the helical track respectively at the intersection between the helical track and the angled track to guide the thread feature into the angled track under an axial force applied to the secondary dose dial component. The angled track may be designed such that the secondary dose dial component is axially guided and cannot rotate during dose dispense of the secondary medicament.

According to a further embodiment, the thread feature overrides the detent feature after a predetermined dose of the primary or the secondary medicament is dialed. Preferably, the thread feature is arranged such that the thread feature overrides the detent feature when the secondary dose dial component is decoupled from the primary dose dial component.

In order to provide the user with a tactile and/or audible feedback during dose setting, the dose setting mechanism may comprise a clutch that is rotationally fixed to the dose dial component during dose setting and a clicker assembly that is configured to engage the clutch in such way that relative rotation between the clutch and the clicker assembly produces a recognizable feedback, such as a click sound and/or a tactile detent, wherein the clicker assembly engages the housing assembly in such way that the clutch rotates with the clicker assembly in the first phase and rotates relative to the clicker assembly in the second phase. The feedback may be the result of a spring of the clicker assembly, striking a projection or the like of the clutch. For example, the spring may be compressed under the force of a projection of the clutch as the clutch rotates relative to the clicker assembly such that the spring is released and recognizable feedback is produced.

The clicker assembly may be configured to move proximally during dose setting and may be axially constrained to the primary drive sleeve which is configured to move proximally during dose setting. The clicker assembly may comprise a key that engages an axially extending groove on the housing assembly by way of a spline connection, wherein the axially extending groove has at least one intermediate section that allows the clicker assembly to disengage from the groove. Thereby, it can be efficiently ensured that the clicker assembly is rotationally locked with respect to the housing assembly in the second phase of the dose setting and is free to rotate relative to the housing assembly in the first phase of the dose setting.

Preferably, the key is configured to disengage from the groove in the first phase of the dose setting, resp. during dose setting of the fixed dose. A reliable indication is delivered to the user that an injectable variable dose of the primary medicament is not being set and that a fixed dose of the secondary medicament is being set.

According to a further embodiment, the clicker assembly is configured to lock the primary drive sleeve against rotation in a first phase during dose dispense and to release the primary drive sleeve in a second phase of the dose dispense such that the primary drive sleeve rotates relative to the housing assembly under an axial force in distal direction. Thereby, the dispense of the primary medicament can be interrupted and a clear separation between the variable dose medicament dispense phase and the fixed dose medicament dispense phase can be realized. This may be achieved by configuring the axial groove on the housing such that the key disengages from the groove when the boss moves from the second section back into the first section during dose dispense.

In order to ensure that the entire secondary medicament is flushed out of the injection needle during the injection process, the groove may also be configured such that the key reengages the groove such that the clicker assembly and the primary drive sleeve are locked against rotation and that the delivery of the variable dose is resumed.

According to a further embodiment, the length of the angled track is chosen such that the thread feature reengages the helical track on the secondary drive sleeve when the key reengages the groove of the housing. Consequently, as the dispense of the primary medicament is resumed, dispense of the secondary medicament is stopped.

In certain aspects, a drug delivery device includes a primary drug delivery assembly for the delivery of a primary medicament and a secondary drug delivery assembly for the delivery of a secondary medicament. The drug delivery device includes a dose setting mechanism as described herein.

The drug delivery device can be a disposable injection device. Such devices can be thrown away or recycled after the content of the medicaments has been exhausted. Certain aspects of the present invention are also applicable with re-usable devices designed to replace an empty cartridge with a filled one after the whole content of the former cartridge has been administered.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antihousing or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antihousing is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antihousing; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antihousing contains two light chains that are always identical; only one type of light chain, κ or λ, is present per antihousing in mammals.

Although the general structure of all antibodies is very similar, the unique property of a given antihousing is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antihousing fragment" contains at least one antigen binding fragment as defined above, and exhibits essentially the same function and specificity as the complete antihousing of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE DRAWINGS

An exemplary embodiment will now be described with reference to the accompanying drawings in which.

DETAILED DESCRIPTION

Figure 1:
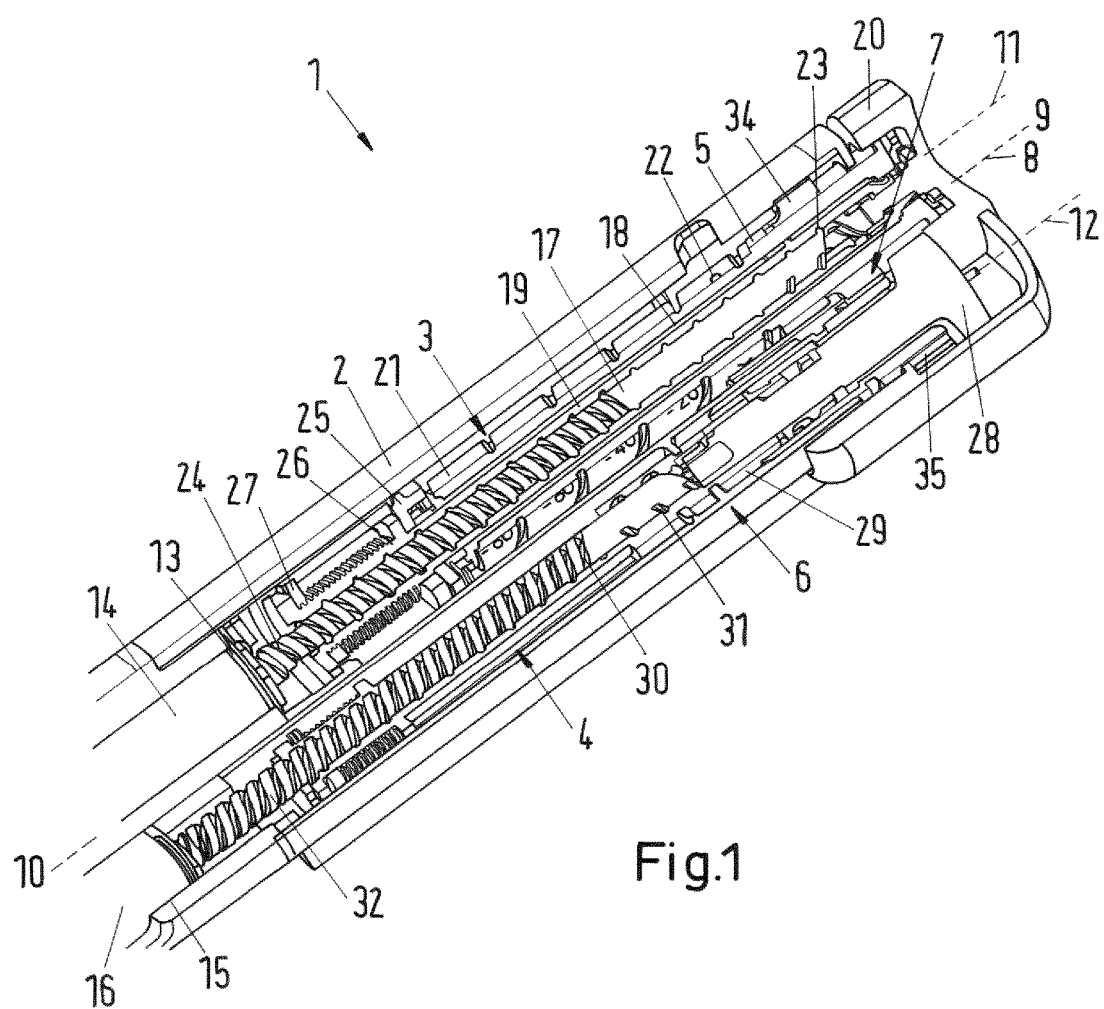
FIG. 1 shows in a perspective sectional view a drug delivery device with the dose setting mechanism.

FIG. 1 gives a three-dimensional cut-away view of a drug delivery device 1 configured as a pen-type injector. The drug delivery device 1 comprises a drug delivery device housing assembly 2 in which a primary drug delivery assembly 3 and a secondary drug delivery assembly 4 are retained.

The drug delivery device 1 further comprises a variable dose mechanism 5 which is associated with the primary drug delivery assembly 3 and a fixed dose mechanism 6 associated with the secondary drug delivery assembly 4 and a gear mechanism 7 that links the two mechanisms 5 and 6. The variable dose mechanism 5 is accommodated in the housing assembly 2, wherein components of the variable dose mechanism 5 can displace out of the housing assembly 2 in proximal direction. The fixed dose mechanism 6 is also accommodated in the housing assembly 2. The drug delivery device 1 is designed to be set and dispensed using the same method as a typical injector used for delivery of a user variable medicament dose, without any additional user steps.

The drug delivery device 1 extends along a longitudinal axis 8 from a proximal end 9 to a distal end 10.

The primary drug delivery assembly 3 extends along a longitudinal axis 11 while the secondary drug delivery assembly 4 extends along a longitudinal axis 12. The longitudinal axes 11 and 12 are parallel offset with respect to the longitudinal axis 8. At the distal end 10 of the primary drug delivery assembly 3, a primary medicament cartridge 13 is located, which is filled with a primary medicament 14, e.g. insulin. At the distal end 10 of the secondary drug delivery assembly 4, a secondary medicament cartridge 15 is located, which contains a secondary medicament 16, e.g. GLP-1.

At the distal end 10 of the drug delivery device 1, a needle hub (not shown) can be attached. Said needle hub comprises a distal injection needle for injecting the medicaments 14, 16 into the patient. Further, the needle hub comprises two proximal needles, each of the needles establishing fluid communication the common injection needle and the respective medicament 14, 16.

The primary drug delivery assembly 3 comprises a primary lead screw 17, a clutch 18 and a primary drive sleeve 19. At the proximal end 9 of the primary drug delivery assembly 3, a dial grip 20 is arranged. Further, the primary drug delivery assembly 3 comprises a primary dose dial component 21, which is configured as a number sleeve and which has a dose volume scale 22 printed on its outer peripheral surface, wherein the dose volume scale 22 extends along a helical pattern on the primary dose dial component 21. At the distal end 10 of the primary lead screw 17, a bearing is located. Upon displacement of the primary lead screw 17 in distal direction, the primary medicament 14 is dispensed from the primary medicament cartridge 13. The primary lead screw 17 is threaded to the primary drive sleeve 19 via a first thread 23 and the primary lead screw 17 is also threaded to the housing assembly 2 via a second thread 24, wherein the first thread 23 and the second thread 24 have opposite orientations, respectively hands. At a distal section of the primary drive sleeve 19, a clicker assembly 25 rests on a radial protrusion 26 of the primary drive sleeve 19 and surrounds the primary drive sleeve 19. A primary last dose nut 27 is threaded to the primary drive sleeve 19 at its distal end.

The secondary drug delivery assembly 4 comprises a fixed dose dispense shaft 28, a secondary dose dial component configured as a secondary drive sleeve 29 and a secondary lead screw 30. The secondary lead screw is threaded to the secondary drive sleeve 29 via a first thread 31 and is threaded to the housing assembly 2 via a second thread 32, the first thread 31 and the second thread 32 having opposite orientations. At the distal end of the secondary drive sleeve 29, a secondary last dose nut 33 is threaded to the secondary drive sleeve 29.

The gear mechanism 7 comprises a first gear 34 and a second gear 35 which are configured to mesh. The first gear 34 is configured to rotate about the longitudinal axis 11 of the primary drug delivery assembly 3, while the second gear 35 is configured to rotate about the longitudinal axis 12 of the secondary drug delivery assembly 4. When the first gear 34 and the second gear 35 are in meshed engagement, rotation of the first gear 34 is transferred to the second gear 35 which is forced to rotate about the longitudinal axis 12 in the opposite rotational direction. The distal end of the secondary lead screw 30 is provided with a bearing. Upon displacement of the secondary lead screw 30 in distal direction, the bearing displaces the secondary medicament 16 in the secondary cartridge 15 such that the secondary medicament 16 is dispensed from the needle hub.

The dial grip 20 has a clutch connection (not shown) to the number sleeve 21 for mutual rotational fixation, which is treaded to the housing assembly 2 such that when the number sleeve 21 is rotated in a first direction (during dose setting), it displaces in proximal direction while being rotated and when the primary dose dial component 21 rotates in the opposite direction (during dose dispensing), it screws back into the housing assembly 2. The number sleeve 21 is also clutched to the clutch 18 during dose setting, which in turn is splined to the primary drive sleeve 19. As indicated above, the primary lead screw 17 is both threaded to the primary drive sleeve 19 and the housing assembly 2 with opposite hand threads. The ratio between the pitches of the threads 23 and 24 determines the mechanical advantage of the variable dose mechanism 5. The thread between the primary drive sleeve 19 and the primary lead screw 17 has an identical pitch to the thread between the number sleeve 21 and the housing assembly 2.

The device 1 is set by rotating the dial grip 20 around the longitudinal axis 11. This also rotates the number sleeve 21, the clutch 18 and the primary drive sleeve 19. This rotation forces the number sleeve 21 to take the helical path provided by the thread interface with the housing assembly 2. The primary drive sleeve 19 takes the helical path provided by the thread interface with the primary lead screw 17. This action results in the dial grip 20, the number sleeve 21, the primary drive sleeve 19 and the clutch to protrude out of the housing assembly 2 in proximal direction. The combined volume of the user variable dose and fixed dose (when set) is communicated to the user via a dose window (not shown) on the housing assembly 2. Said window aligns with the relevant number of the dose volume scale 22 on the number sleeve 21 to ensure the correct dose is always shown during setting and dispensing.

During dialing, the user feels a tactical detent and hears an audible click between available dose sizes, provided by a continued engagement and disengagement of the dial clicker assembly 25 in castellations on the clutch 18.

Figure 2:
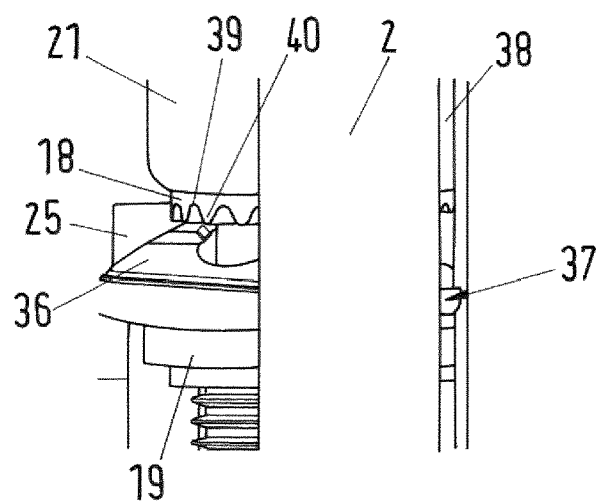
FIG. 2 shows in a side view a section of the variable dose mechanism.

As shown in FIG. 2, the clicker assembly 25 is arranged on the primary drive sleeve 19 and comprises a spring 36 and a key 37. The key 37 is splined to the housing assembly 2. The housing assembly 2 comprises an axially extending groove 38. When the key 37 is engaged with the groove 38, the clicker assembly 25 and the spring 36 are locked from rotation. The detent and click feedback are the result of the spring 36 striking a castellation trough 39 of the clutch 18 that is partially located in the number sleeve 21 when released from compression under a castellation peak 40, as the clutch 18 rotates relative to the clicker assembly 25.

A fixed dose of the secondary medicament 16 is automatically set, when a dose greater than a 'priming' volume is set with the variable dose medicament 5. This allows the user to prime the needle without dispensing any fixed dose medicament, while ensuring that any dose of the variable dose medicament larger than a prime dose is dispensed with a dose of the fixed dose medicament. The fixed dose is set with a pre-defined rotation of the dial grip 20. During this rotation, the scale 22 on the number sleeve 21 communicates to the user to continue rotating the dial grip 20, via suitable symbols (arrows, etc.). The rotation required to set the fixed dose is translated to the fixed dose mechanism via the gear mechanism 7.

Figure 3:
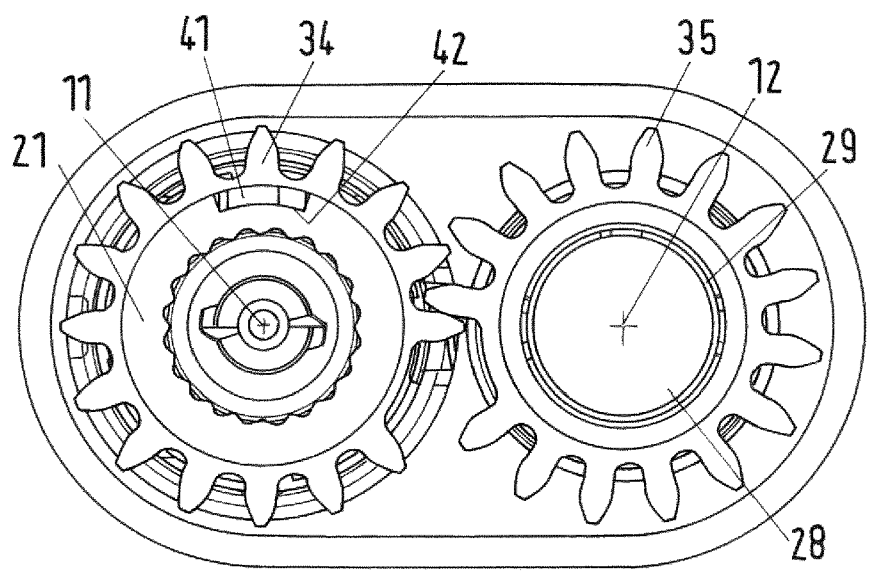
FIG. 3 shows in a plane view the gear mechanism.

As shown in FIG. 3, which illustrates the proximal section of the drug delivery device 1 in a cut-view when looking from the proximal end of the device to the distal end, the first gear 34 is in meshed engagement with the second gear 35 and both are rotatable around the respective axis 11, 12. The first gear 34 is substantially coaxially arranged on the number sleeve 21 and comprises a boss 41 on a radial inner surface, res. an inner diameter. The boss 41 is engaged with a track 42 in the outer surface of the number sleeve 21, which is moveable in the axial direction with respect to the first gear 34, depending on the engagement between the boss 41 and the track 42. The second gear 35 surrounds the fixed dose dispense shaft 28 and a distal section of the secondary drive sleeve 29. When the second gear 35 is rotated, a dose of the secondary medicament is set in the fixed dose mechanism. The proximal end of the secondary drive sleeve 29 has a spring feature 51 (FIG. 5) which biases against a distally oriented surface on the fixed dose dispense shaft 28, which is urged in into a raised position, resp. proximal position with respect to the secondary drive sleeve 29.

Figure 4A:
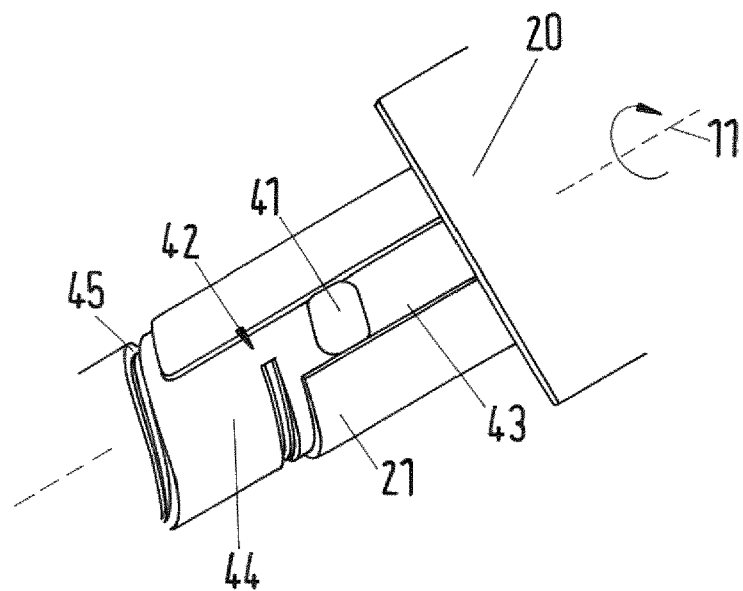
FIGS. 4a, 4b show in side views another section of the variable dose mechanism during dose setting.
Figure 4B:
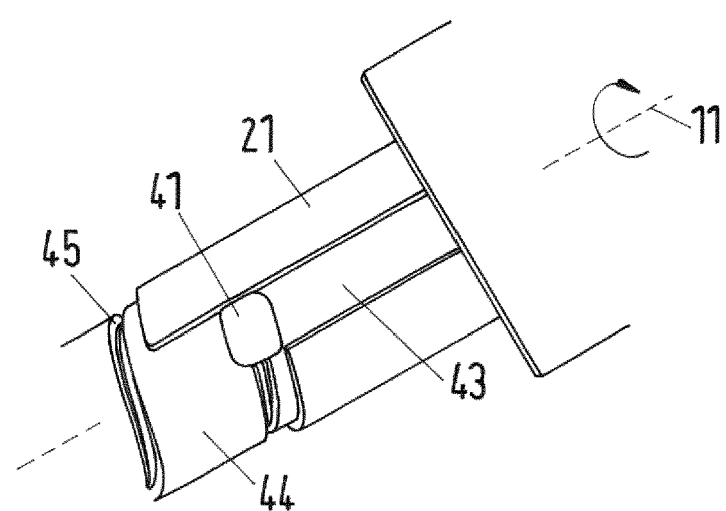

In FIGS. 4 and 4b, the engagement between the number sleeve 21 and the boss 41 of the first gear 34 during dose setting is illustrated. The dose setting process includes a first dose setting phase (FIG. 4a) and a second dose setting phase (FIG. 4b). In the first phase of the dose setting, the first gear is rotationally coupled to the number sleeve 21, such that rotation of the dial grip 20 is transferred through the number sleeve 21 to the first gear 34. The track 42 on the number sleeve 21 comprises a first section 43 and a second section 44. In the first section 43, the track extends in axial direction of the number sleeve 21, thereby forming a key or splined connection with the first gear 34 such that when the number sleeve 21 is rotated in clockwise direction as indicated by the arrow, this rotation is transferred to the first gear 34 while the number sleeve 21 displaces relative to the first gear 34 in proximal direction and the boss 41 travels from the first section 43 into the second section 44. At this point, the subsequent second phase of the dose setting is initiated. In this phase, rotation of the number sleeve 21 is not transferred to the second gear 35 so that no dose setting takes place in the secondary drug delivery assembly. Displacement of the number sleeve 21 upon rotation is caused by the thread engagement with the housing assembly 2, which includes a helical groove 45 on the outer surface of the number sleeve 21.

The second section 44 is formed such that the number sleeve 21 can rotate relative to the first gear 34 so that rotational movement is not transferred to the first gear 34. For example, the second section 44 may be formed such that it extends along the number sleeve 21 along a helical path, parallel to the helical groove 45. The first section 43 and the second section 44 are arranged such that the boss 41 enters the second section 44 after a predetermined axial displacement of the number sleeve 21, which corresponds to a predetermined set dose of the primary medicament and/or of the second medicament. This connection ensures that the first gear 34 is locked in rotation to the dial grip 20 during the setting of a prime dose (pre-defined) in the primary drug delivery assembly and a fixed dose (pre-defined) in the secondary drug delivery assembly. The fixed dose is set as long as the first gear 34 is engaged with the number sleeve 21. Once the fixed dose is set, the first track section 43 disengages from the boss ensuring that any further setting of the variable dose will not rotate the gear system. At this point fixed dose setting is finished and the user may rotate the dose dial 20 further to set a higher (variable) dose of the primary medicament.

Figure 5:
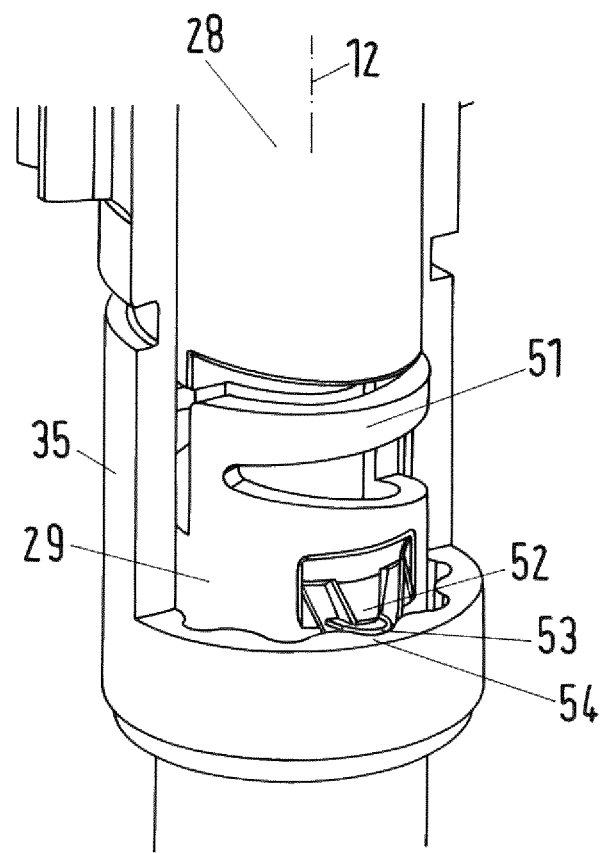
FIG. 5 shows in a side view a section of the fixed dose mechanism.

With respect to FIG. 5, the fixed dose dispense shaft 28 is splined to the housing assembly and seated on the spring features 51 on the secondary drive sleeve 29. The outer diameter of the secondary drive sleeve 29 has flexible arms 52 with protruding clutch features 53. When the second gear 35 rotates, the spring features 51 bias the fixed dose dispense shaft 28 into a raised position, which locks the flexible arms 52 from deforming towards the centre line 12 of the fixed dose mechanism. This in turn locks the secondary drive sleeve 29 in rotation to the second gear 35 and therefore the dial grip 20 via the engagement of the clutch features 53 with the spline features 54 on the inner diameter of the second gear 35.

The secondary lead screw 30 is both threaded to the secondary drive sleeve 29 and the housing assembly 2 with the opposite threads 31, 32 (FIG. 1). The ratio between the pitches of these threads determines the theoretical mechanical advantage of the fixed dose delivery. The thread between the secondary drive sleeve 29 and secondary lead screw 30 is equal to the pitch of the thread between the primary drive sleeve 19 and primary lead screw 17 divided by the ratio between the first gear 34 and the second gear 35. This mathematical relationship ensures that the dial grip 20 and fixed dose dispense shaft 28 maintain a relative vertical position during setting and dispensing of both the prime dose and the fixed dose element.

When the secondary drive sleeve 29 is rotated via the second gear 35 during setting, the secondary drive sleeve 29 takes the helical path provided by the thread interface with the secondary lead screw 30. The secondary drive sleeve 29 is also rotated during setting of the prime dose, however this extra rotation is reversed during dispense of the prime dose (described later).

Figure 6A:
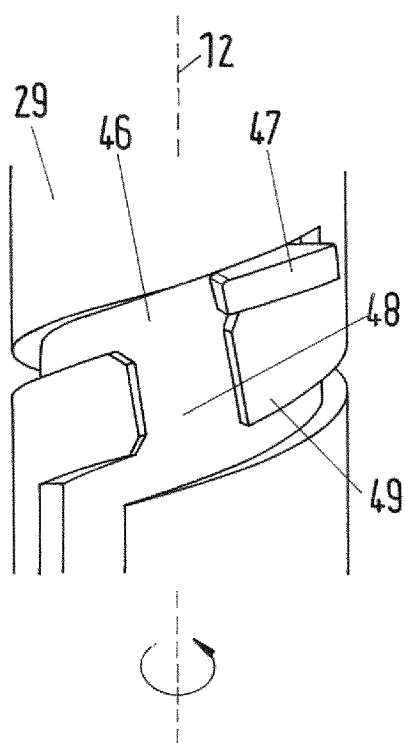
FIGS. 6a 6b show in side views another section of the fixed dose mechanism.

As shown in FIG. 6a, the outer surface of the secondary drive sleeve 29 is provided with a helical track 46 that is engaged by a thread feature 47 on the inner surface of the housing assembly 2. Preferably, there are two thread features engaging the secondary drive sleeve. As the secondary drive sleeve 29 is rotated in the first phase, the thread feature 47 on the inside of the housing assembly 2 follows the track 46 on the secondary drive sleeve 29 into the position shown in FIG. 6b.

The helical track 46 is intersected by an angled track 48 or angled path. When the thread feature 47 is in the angled track 48, relative rotation between the secondary drive sleeve 29 and the thread feature 47 is prevented.

At the intersection between the angled track and the helical track 46, at least one detent feature 49 is formed. When the fixed dose is set, the secondary drive sleeve 29 is rotated in counterclockwise direction when looking from the proximal end to the distal end as indicated by the arrow. This causes the thread feature 47 to travel along the helical track 46 until the fixed dose is fully set. At this point, the thread feature 47 overrides the detent 49 on the track and the second phase of the dose setting begins. The secondary drive sleeve 29 is no longer rotated as the first gear disengages from the number sleeve.

The detent features 49 aid delivery (described later) and provide tactile communication to the user that the device has entered the subsequent second phase of the dose setting. Unsetting the device requires the user to overcome the detent.

As indicated above, the mechanism is designed to rotate the secondary drive sleeve 29 by the theoretical rotation required to set the fixed dose. This is the rotation required to raise the secondary drive sleeve 29, using the thread interface with the secondary lead screw 30, by the secondary lead screw 30 advancement required to dispense a dose multiplied by the theoretical mechanical advantage.

Figure 6B:
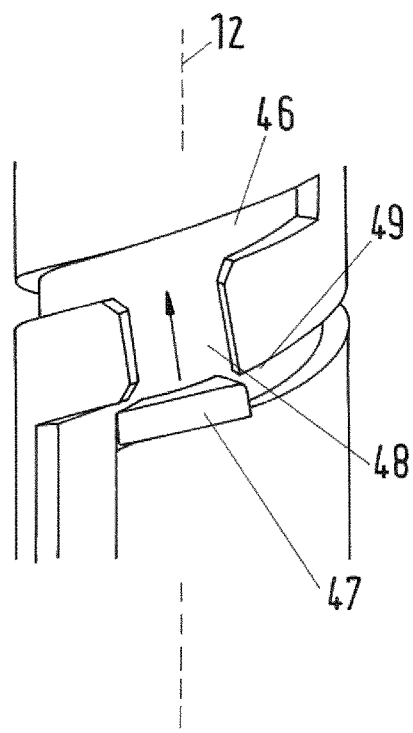

In practice, the rotation required is less due to the dispense path being angled, rather than vertical. As can be seen in FIG. 6b, the secondary drive sleeve 29 is rotated such that the opening of the angled track 48 is moved slightly past the thread feature 47. This ensures that the fixed dose is fully set (in all tolerance conditions and with consideration of backlash in the gear system) before the first gear 34 disengages the number sleeve 21 and stops rotating.

The outer diameter of the distal section of the fixed dose dispense shaft has two flexible arm features with outwardly protruding teeth. These teeth engage with spline features on the secondary drive sleeve 29 inner diameter. When the secondary drive sleeve 29 rotates relative to the fixed dose dispense shaft 28 during setting and unsetting, the flexible arms are deformed radially inwards by peaks of the spline features and then allowed to relax into troughs of the spline features. When the arms relax, they strike the surface of the trough, giving a tactile detent and an audible 'click' to the user.

Whilst setting the fixed dose, the variable dose mechanism is theoretically dialing part of the variable dose, since the primary drive sleeve 19 moves relative to the primary lead screw 17. However the additional volume dialed during this period is effectively undialed during dispense (described later) and therefore no extra variable dose fluid is dispensed.

Figure 7:
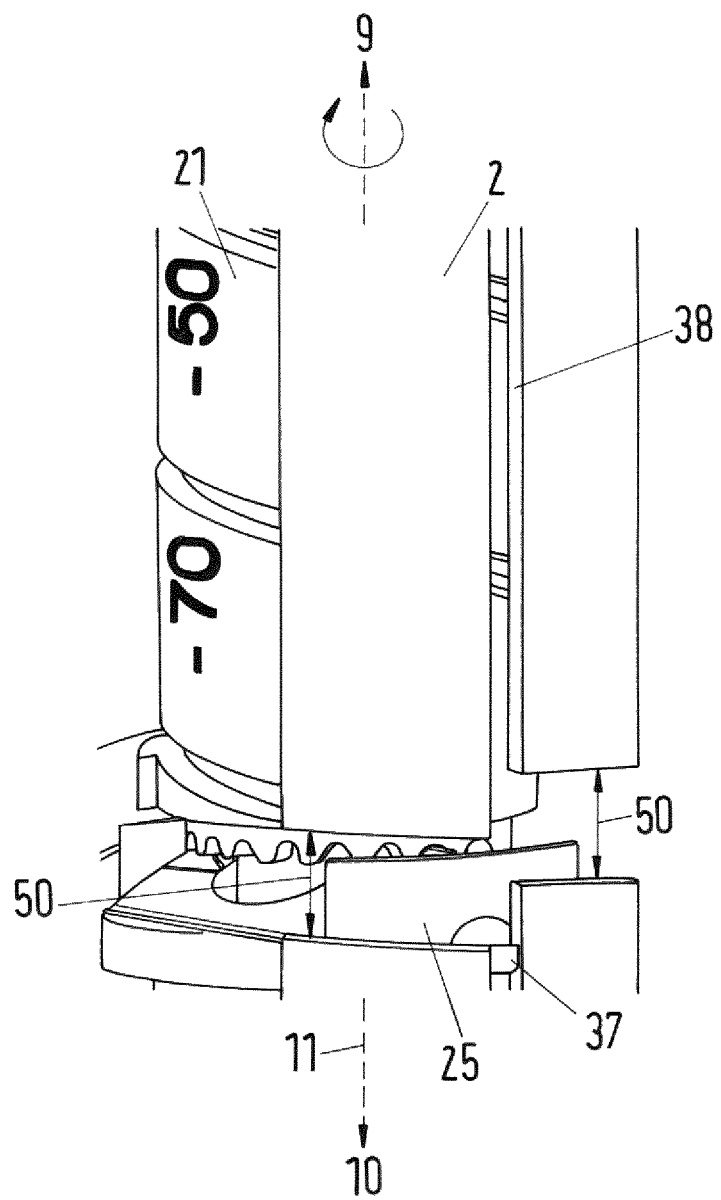
FIG. 7 shows in a side view another section of the variable dose mechanism.

As shown in FIG. 7, which is a side view on components of the variable dose mechanism, the axial groove 38 on the housing assembly 2 is interrupted by an intermediate section 50. During dose setting, when the number sleeve 21 is rotated in clockwise direction as indicated by the arrow, the clicker assembly 25 moves in proximal direction 9. During the setting the fixed dose mechanism, the clicker assembly 25 enters the portion 50 of the housing assembly 2 where there is no spline to engage with. During this period, the clicker assembly 25 is allowed to rotate with the clutch and primary drive sleeve 19. This ensures that during setting of the fixed dose, no tactile detent or audible click is produced by the variable dose mechanism.

The injector can be dialed back to the original rest position from any point in the setting sequence. The user achieves this by rotating the dial grip 20 in the opposite direction to setting. Un-setting the device produces the opposite relative movements between the components, in the reverse sequence, as performed during setting.

The user dispenses the combined dose by applying an axial force on the dial grip 20 in distal direction. Initially the force follows a load path through the dial grip 20 and clutch 18, which move towards the primary medicament cartridge 13, compressing the spring 36 (FIG. 2) of the clicker assembly 25. This movement declutches the number sleeve 21 from the dial grip 20 and the clutch 18.

Whilst the spring is compressed, the clutch 18 is effectively coupled to the clicker assembly 25 and therefore locked from rotation due to the spline interface between the key and the housing assembly 2. This means that the primary drive sleeve 19 is also locked from rotation due to the spline connection with the clutch 18.

As the user forces the dial grip 20 and clutch 18 towards the primary medicament cartridge 13 (FIG. 1), the dial grip 20 first contacts the number sleeve 21, which begins to retract into the housing assembly 2, towards the primary medicament cartridge 13, along the same helical path used during setting. Second, the dial grip 20 contacts the primary drive sleeve 19, now locked from rotation, applying the axial force directly to it. As the primary drive sleeve 19 moves axially, the threaded connection to the primary lead screw 17 causes the primary lead screw 17 to rotate.

The primary lead screw 17 then advances axially as it is rotated through the thread interface within the housing assembly 2. The primary lead screw 17 then imparts a force onto the primary medicament cartridge bung, causing fluid to be dispensed. The ratio between primary drive sleeve 19 and primary lead screw 17 advancement is the mechanical advantage of the variable dose dispense and is set by the pitches of the two threads 23, 24 on the primary lead screw 17.

During dispense of the variable dose element, the number sleeve 21 rotates relative to the clutch 18. The clutch 18 has two flexible arms with clutch features (not shown) that protrude from the outer diameter. These clutch features interface with spline features on the inner diameter of the number sleeve 21. When relative rotation occurs, the flexible arms are deformed inwards, towards the centre line of the variable dose mechanism, by peaks of the spline features and then allowed to relax into troughs. When the arms relax, they strike the surface of the trough, giving a tactile detent and an audible click to the user during dispense.

When only the prime dose of the variable dose element is remaining to be dispensed the drug delivery device stops dispensing the variable dose medicament and enters the fixed dose dispense phase. This is the dialing sequence in reverse. The dispense of the variable dose is paused by allowing the primary drive sleeve 19 to rotate down the helical path on the primary lead screw 17 thread interface, effectively un-dialing this section of the dose. The primary drive sleeve 19 becomes free to rotate due to the clicker assembly 25 entering the intermediate section 50 of the groove 38 on the housing assembly 2 that has no spline to engage with (previously shown in FIG. 7).

Figure 8A:
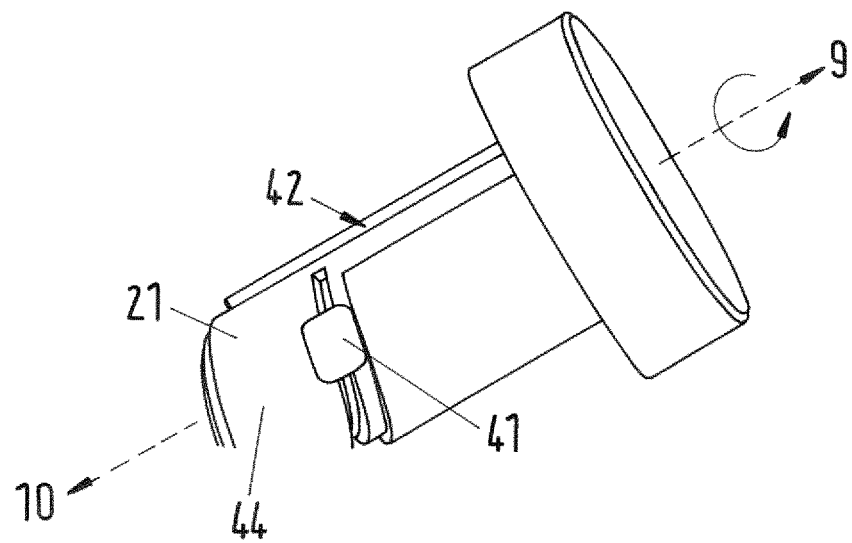
FIGS. 8a, 8b show in side views the section of FIGS. 4a and 4b during dose dispense.
Figure 8B:
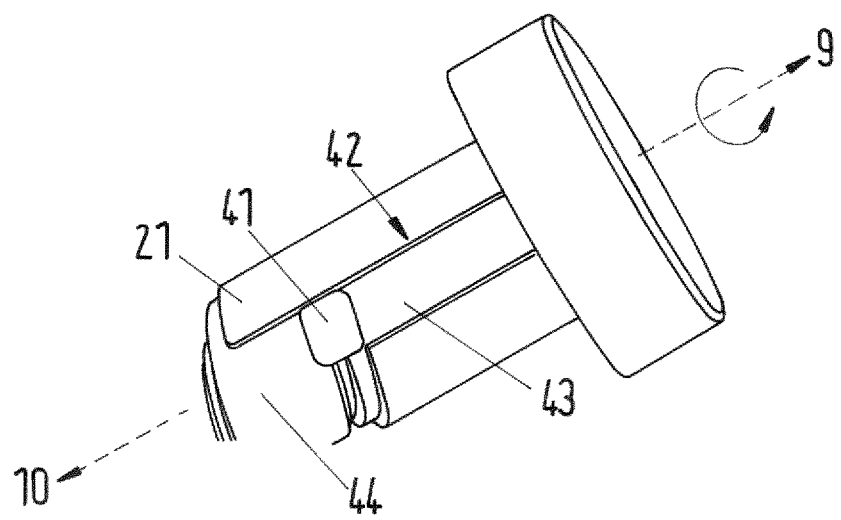

In FIGS. 8a and 8b, the engagement between the boss 41 and the number sleeve 21 during dispense in the fixed dose mechanism is shown in a side view. The number sleeve 21 moves in distal direction 10 during dose dispense relative to the boss 41 in a helical movement as indicated by the arrow. As the drug delivery device 1 enters the fixed dose dispense phase, the boss 41 leaves the second section 44 and the first section 43 of the track 42 reengages with the boss 41 of the first gear 34 (FIG. 8b). This locks the first gear 34 in rotation to the number sleeve 21 for the rest of dispense (fixed dose and prime dose of the variable dose). Rotation of the second gear 35 is also initiated at this time through the gear mechanism.

The fixed dose dispense is initiated when the dial grip 20 applies an axial force on the fixed dose dispense shaft 28. The force applied moves the fixed dose dispense shaft 28 in distal direction compressing the spring features 51 on the distal end of the secondary drive sleeve 29 that the fixed dose dispense shaft 28 is seated on (FIG. 5). The fixed dose dispense shaft 28 contacts the secondary drive sleeve 29 end face, applying the user force directly to it.

Under an axial load the secondary drive sleeve 29 would naturally take the helical path provided by the thread interface with the secondary lead screw 30 (unsetting the fixed dose element). This is due to the torque induced by contact forces generated at this thread interface. However, the torque produced is not sufficient to allow the thread features 47 (FIG. 6b) on the inside of the housing assembly 2 to override the detent feature 49. Instead the secondary drive sleeve 29 is forced to take the dispense path (angled track), wherein the secondary drive sleeve 29 is guided by the thread features 47 on the inside of the housing assembly 2 as indicated by the arrow.

The detent 49 can be overridden to unset the device by the application of a direct torque to the secondary drive sleeve 29 via the dial grip 20, number sleeve 21 and the gear system. The fixed dose is fully dispensed when the thread feature 47 exits the angled track 48 and returns to the helical portion 46 that is used during setting.

Since the secondary drive sleeve 29 is guided down the dispense path 48, the torque generated at the thread interface with the secondary lead screw 30 forces the secondary lead screw 30 to rotate. This rotation advances the secondary lead screw 30 through the thread in the housing assembly 2, but also allows the secondary drive sleeve 29 to advance relative to the secondary lead screw 30. The ratio between secondary drive sleeve 29 and secondary lead screw 30 advancement is the mechanical advantage of the fixed dose dispense.

During dispense of the fixed dose, the secondary drive sleeve 29 takes the dispense path (previously described) and the second gear 35 is rotated via the dial grip 20, number sleeve 21 and first gear 34. During setting the two are locked in rotation due to clutch features on flexible arms on the secondary drive sleeve 29 engaging with spline features on the inner diameter of the second gear 35. This occurs because the fixed dose dispense shaft 28 is in a raised position and locks the flexible arms from deforming inwards, towards the centre line of the fixed dose mechanism. At the start of fixed dose dispense, the fixed dose dispense shaft is forced into a distal position, allowing the flexible arms to deform. When the second gear 35 rotates relative to the secondary drive sleeve 29, the flexible arms are deformed inwards by peaks of the spline features and then allowed to relax into troughs of the spline features. When the arms relax, they strike the surface of the trough, giving a tactile detent and an audible click to the user.

In the following, it is explained how a prime dose is dispensed with respect to FIG. 2. When the fixed dose element is fully dispensed, the delivery of the variable dose resumes and the prime dose is dispensed. This is achieved by the movement of the key of the clicker assembly 25 in distal direction. The key 37 re-engages with splines, resp. the groove 38 on the housing assembly 2, locking the primary drive sleeve 19 against rotation. Therefore, the primary lead screw 17 is forced to rotate and hence the primary lead screw 17 advances through the thread interface with the housing assembly in distal direction such that the primary medicament is dispensed.

With reference to FIG. 6b, during dispense of the 'prime' dose (or the last 2 units of a larger variable dose), the dial grip 20 is in contact with the fixed dose dispense shaft, which is in contact with the secondary drive sleeve 29. Therefore an axial force is still being applied to the secondary drive sleeve 29. However, when the fixed dose is dispensed, the thread element 47 has reentered the helical track 46 on the secondary drive sleeve 29 and is no longer in the angled track 48 forming the dispense path. This allows the secondary drive sleeve 29 to advance along the helical track 46 provided by the interface with the secondary lead screw 30, without advancing the secondary lead screw 30.

The variable dose and the fixed dose mechanisms are designed to lock the device 1 from setting when the relevant cartridge 13 or 15 is expended. This is achieved by locking the relevant drive sleeve 19 or 29 from rotation after a pre-defined total number of rotations in the setting direction have occurred. In the variable dose mechanism 5, the primary last dose nut 27 (see FIG. 1) performs this locking function. The primary last dose nut 27 is threaded to the primary drive sleeve 19 and is locked in rotation to the clicker assembly 25 via a spline connection that extends in axial direction. During setting, the primary drive sleeve 19 rotates relative to the primary last dose nut 27 forcing the primary last dose nut 27 to move towards the dial grip 20 relative to the primary drive sleeve 19 along the thread interface. During dispense the primary drive sleeve 19 is locked from rotation. Therefore, there is no movement of the primary last dose nut 27 relative to the primary drive sleeve 19. During the un-setting of a dose, the primary drive sleeve 19 rotates in the reverse direction to setting, therefore the advancement of the primary last dose nut 27 that occurred during setting is reversed. When the total volume of medicament set is equal to the volume of medicament that a new cartridge contains, the primary last dose nut 27 comes into contact with rotational stops on the primary drive sleeve 19, locking the rotation of the primary drive sleeve 19.

During the set and dispense (or unset) of the fixed dose, the variable dose is set and unset (previously described). This action does not advance the primary last dose nut 27, as there is no relative movement with primary drive sleeve 19. This is due to the clicker assembly 25, and therefore the primary last dose nut 27, being free to rotate with the primary drive sleeve 19 during this period.

In the fixed dose mechanism 6, the secondary last dose nut 33 performs the locking function. The secondary last dose nut 33 is threaded to the secondary drive sleeve 29 and is locked in rotation to the housing assembly 2 via a spline connection. During setting, the secondary drive sleeve 29 rotates relative to the secondary last dose nut 33 forcing the secondary last dose nut 33 to move towards the fixed dose dispense shaft 28 relative to the secondary drive sleeve 29 along the thread interface. During dispense the secondary drive sleeve 29 is forced to take the dispense path (previously described). Taking this angled dispense path actually sets the remainder of the theoretical dose while dispensing. The setting component further advances the secondary last dose nut 33 via relative rotation between the secondary last dose nut 33 and the secondary drive sleeve 29. The dispense component does not advance the secondary last dose nut 33 as there is no relative rotation. During the un-setting of a dose, the secondary drive sleeve 29 rotates in the reverse direction to setting, therefore the advancement of the secondary last dose nut 33 that occurred during setting is reversed. When the net volume of medicament set is equal to the volume of medicament that a new cartridge contains, the secondary last dose nut 33 comes into contact with rotational stops on the secondary drive sleeve 29, locking the rotation of the secondary drive sleeve 29.

The variable dose mechanism and the fixed dose mechanism may each be at least partly accommodated in a housing sub-assembly with the respective medicament cartridge, which are configured for mutual attachment. If one of the cartridges is expended, the respective sub-assembly may be discarded and replaced. Preferably, the only interface that connects the subassemblies are simple spline connections between the secondary drive sleeve and the second gear and the secondary drive sleeve and the dispense shaft.

REFERENCE NUMERALS 1 drug delivery device
2 housing assembly
3 primary drug delivery assembly
4 secondary drug delivery assembly
5 variable dose mechanism
6 fixed dose mechanism
7 gear mechanism
8 longitudinal axis
9 proximal end
10 distal end
11 longitudinal axis of primary drug delivery assembly
12 longitudinal axis of secondary drug delivery assembly
13 primary medicament cartridge
14 primary medicament
15 secondary medicament cartridge
16 secondary medicament
17 primary lead screw
18 clutch
19 primary drive sleeve
20 dial grip
21 primary dose dial component (primary number sleeve)
22 dose volume scale
23 first thread
24 second thread
25 clicker assembly
26 radial protrusion
27 primary last dose nut
28 fixed dose dispense shaft
29 secondary dose dial component (secondary drive sleeve)
30 secondary lead screw
31 first thread
32 second thread
33 secondary last dose nut
34 first gear
35 second gear
36 spring
37 key
38 axially extending groove
39 castellation trough
40 castellation peak
41 boss
42 track
43 first track section
44 second track section
45 helical groove
46 helical track on secondary drive sleeve
47 thread feature
48 angled track (dispense path)
49 detent feature
50 intermediate section
51 spring feature
52 flexible arms
53 clutch feature
54 spline feature

The invention claimed is:

1. A dose setting mechanism for a drug delivery device, the dose setting mechanism comprising:
    a primary dose dial component for setting a primary dose in a primary drug delivery assembly of the drug delivery device; and
    a secondary dose dial component for setting a secondary dose in a secondary drug delivery assembly of the drug delivery device, wherein the primary dose dial component and the secondary dose dial component are configured to rotate during dose setting; and
    a gear mechanism configured such that
        rotation of the primary dose dial component is transferred to the secondary dose dial component during a first phase of the dose setting, and
        the secondary dose dial component is decoupled from the primary dose dial component during a second phase of the dose setting, thereby inhibiting rotation of the primary dose dial component from being transferred to the secondary dose dial component, for further setting the primary dose in the primary drug delivery assembly without changing the secondary dose in the secondary drug delivery assembly.

2. The dose setting mechanism according to claim 1, wherein the gear mechanism comprises a first gear coupled to the primary dose dial component such that
    the primary dose dial component is rotationally locked to the first gear during the first phase of the dose setting, and
    the primary dose dial component is rotationally decoupled from the first gear during the second phase of the dose setting.

3. The dose setting mechanism according to claim 2, wherein the gear mechanism comprises a second gear that is in meshed engagement with the first gear and that is rotationally coupled to the secondary dose dial component during the dose setting.

4. The dose setting mechanism according to claim 2, wherein the first gear comprises a boss engaged with a track on the primary dose dial component to transfer rotation between the primary dose dial component and the first gear.

5. The dose setting mechanism according to claim 4, wherein:
    the track comprises a first section and a second section,
    the boss is engageable with the first section until a predetermined dose is set with the primary dose dial component or the secondary dose dial component, and
    the boss is engageable with the second section after the predetermined dose is dialed with the primary dose dial component or the secondary dose dial component.

6. The dose setting mechanism according to claim 5, wherein the second section is engageable with the boss to rotationally decouple the primary dose dial component from the first gear.

7. The dose setting mechanism according to claim 5 wherein the second section extends along a helical path on the primary dose dial component.

8. The dose setting mechanism according to claim 1, wherein:
the primary dose dial component is rotationally fixed to a primary drive sleeve that is in threaded engagement with a primary lead screw via a primary first thread, and
the primary lead screw is in threaded engagement with a housing assembly via a primary second thread.

9. The dose setting mechanism according to claim 8, wherein:
the secondary dose dial component is in threaded engagement with a secondary lead screw via a secondary first thread, and
the secondary lead screw is in threaded engagement with the housing assembly via a secondary second thread.

10. The dose setting mechanism according to claim 9, wherein a pitch of a thread between a secondary drive sleeve and the secondary lead screw is equal to a pitch of a thread between the primary dose dial component and the primary lead screw divided by a gear ratio between a first gear and a second gear.

11. The dose setting mechanism according to claim 1, wherein:
the secondary dose dial component comprises a helical track engaged by a thread feature of a housing assembly,
the secondary dose dial component comprises at least one angled track intersecting the helical track, the at least one angled track being arranged such that after the dose setting the thread feature is guided along the at least one angled track under an axial force applied to the secondary dose dial component.

12. The dose setting mechanism according to claim 11, wherein the helical track comprises at least one detent feature arranged between the at least one angled track and the helical track.

13. The dose setting mechanism according to claim 12, wherein the thread feature overrides the at least one detent feature when a predetermined dose is dialed.

14. The dose setting mechanism according to claim 1, further comprising:
a clutch that is rotationally fixed to the primary dose dial component during the dose setting,
a clicker assembly configured to engage the clutch in such a way that relative rotation between the clutch and the clicker assembly produces a click sound and/or a tactile feedback, the clicker assembly engaging a housing assembly such that the clutch rotates with the clicker assembly during the first phase and relative to the clicker assembly during the second phase.

15. The dose setting mechanism according to claim 14, wherein:
the clicker assembly is configured to move proximally during the dose setting and comprises a key that engages an axially extending groove on the housing assembly, and
the axially extending groove has at least one intermediate section that allows the clicker assembly to disengage from the axially extending groove.

16. The dose setting mechanism of claim 1, wherein:
the gear mechanism comprises a first gear coupled to the primary dose dial component, the first gear comprising a boss engaged with a track on the primary dose dial component to transfer rotation between the primary dose dial component and the first gear, and a second gear that is in meshed engagement with the first gear and that is rotationally coupled to the secondary dose dial component during the dose setting,
the track comprises a first section and a second section,
the boss is configured to engage with the first section during the first phase of the dose setting such that the primary dose dial component is rotationally locked to the first gear and rotation of the primary dose dial component is transferred to the secondary dose dial component such that the secondary dose in the secondary drug delivery assembly is automatically set until a predetermined dose is set with the primary dose dial component or the secondary dose dial component, and
the boss is configured to engage with the second section after the predetermined dose is dialed, wherein the second section is adapted such that engagement of the boss with the second section rotationally decouples the primary dose dial component from the first gear such that rotation of the primary dose dial component is prevented from being transferred to the secondary dose dial component during the second phase of the dose setting.

17. A drug delivery device comprising:
a primary drug delivery assembly for delivery of a primary medicament; and
a secondary drug delivery assembly for delivery of a secondary medicament, and
a dose setting mechanism comprising
a primary dose dial component for setting a primary dose in the primary drug delivery assembly; and
a secondary dose dial component for setting a secondary dose in the secondary drug delivery assembly, wherein the primary dose dial component and the secondary dose dial component are configured to rotate during dose setting, and
a gear mechanism configured such that
rotation of the primary dose dial component is transferred to the secondary dose dial component during a first phase of the dose setting, and
the secondary dose dial component is decoupled from the primary dose dial component during a second phase of the dose setting, thereby inhibiting rotation of the primary dose dial component from being transferred to the secondary dose dial component, for further setting the primary dose in the primary drug delivery assembly without changing the secondary dose in the secondary drug delivery assembly.

18. A method of operating a drug delivery device, the method comprising:
setting a dose of a primary medicament to be delivered from the drug delivery device and a dose of a secondary medicament to be delivered from the drug delivery device, the dose of the primary medicament being adjustable and the dose of the secondary medicament being fixed, wherein the dose of the primary medicament and the dose of the secondary medicament are set during a first phase of dose setting;
adjusting the dose of the primary medicament during a second phase of the dose setting; and
dispensing a combined dose from the drug delivery device, the combined dose including the dose of the primary medicament and the dose of the secondary medicament,
wherein the first phase of dose setting includes causing the rotation of a primary dose dial component to transfer to a secondary dose dial component, and
wherein the second phase of dose setting includes causing the secondary dose dial component to decouple from the primary dose dial component such that rotation of the primary dose dial component is inhibited from being transferred to the secondary dose dial component, for further setting the dose in a primary drug delivery assembly without changing the dose in a secondary drug delivery assembly.

19. The method according to claim 18, wherein setting the dose of the primary medicament and the dose of the secondary medicament comprises operating a single dose setting device.

\* \* \* \* \*